(12) United States Patent
Beebe et al.

(10) Patent No.: US 7,562,562 B2
(45) Date of Patent: Jul. 21, 2009

(54) METHOD AND DEVICE FOR DETECTING A MATERIAL

(75) Inventors: David J. Beebe, Monona, WI (US); Dongshin Kim, Champaign, IL (US)

(73) Assignee: Wisconsin Alumni Research Foundation, Madison, WI (US)

( * ) Notice: Subject to any disclaimer, the term of this patent is extended or adjusted under 35 U.S.C. 154(b) by 91 days.

(21) Appl. No.: 11/745,855

(22) Filed: May 8, 2007

(65) Prior Publication Data

US 2008/0276718 A1    Nov. 13, 2008

(51) Int. Cl.
*G01N 33/48* (2006.01)
*G01N 3/08* (2006.01)

(52) U.S. Cl. ........................................ 73/61.43; 73/827
(58) Field of Classification Search ............... 73/150 A, 73/61.41, 61.43, 827, 834, 838; 340/603–605; 156/64, 378
See application file for complete search history.

(56) References Cited

U.S. PATENT DOCUMENTS

| 4,491,014 A | * | 1/1985 | Seiler, Jr. ................... 73/150 A |
| 4,631,952 A | * | 12/1986 | Donaghey .................. 73/25.03 |
| 4,806,312 A | * | 2/1989 | Greenquist .................. 422/56 |
| 5,120,665 A | * | 6/1992 | Tsukagoshi et al. ........... 156/64 |
| 5,673,586 A | * | 10/1997 | Mann ........................ 73/150 A |
| 5,768,936 A | * | 6/1998 | Mann ........................ 73/150 A |
| 7,112,304 B2 | * | 9/2006 | Starling et al. ................ 422/83 |
| 2004/0050152 A1 | * | 3/2004 | King ........................ 73/150 A |

* cited by examiner

*Primary Examiner*—John Fitzgerald
(74) *Attorney, Agent, or Firm*—Boyle Fredrickson, S.C.

(57) ABSTRACT

A method and device is provided for detecting a predetermined material. The device includes a first inner layer having first and second surfaces and a volume responsive to a first predetermined stimuli. A second inner layer has first and second surfaces. An adhesive bonds at least a portion of the first surface of the first inner layer to the first surface of the second inner layer with a bonding force. A change in the volume of the first layer generates an elastic force on the adhesive material. As a result, the first inner layer delaminates from the second inner layer in response to the elastic force overcoming the bonding force.

19 Claims, 3 Drawing Sheets

METHOD AND DEVICE FOR DETECTING A MATERIAL

REFERENCE TO GOVERNMENT GRANT

This invention was made with United States government support awarded by the following agencies: NAVY N00014-04-1-0659. The United States has certain rights in this invention.

FIELD OF THE INVENTION

This invention relates generally to detection systems, and in particular, to a real time method and device for detecting a material, such as a toxin or other chemical compound, in an aqueous environment.

BACKGROUND AND SUMMARY OF THE INVENTION

Most present biosensors take advantage of biologically active materials for high sensitivity and selectivity. In general, these biosensors include a bio-recognition structure (e.g., a membrane) in contact with or interrogated by a transducer. The biologically active material recognizes a particular biological molecule through a reaction, specific adsorption, or other physical or chemical process, and the transducer converts the output of this recognition into a usable signal, usually electrical or optical. Many approaches have been explored to achieve ultra-sensitive detection of bio-species. These biodetection approaches can be categorized as either an engineering-oriented approach or a biological-oriented approach. In other words, most biodetection schemes are either based on relatively complex electronic, photonic and/or electrochemical methods or on more elegant biomolecular methods (e.g. enzyme linked immunosorbent assay, or ELISA) typically with an optical or spectrometry-based readout. In view of the foregoing, there has been an enormous effort in recent years to develop practical and cost-effective biosensors.

In seeking a solution to a human problem, scientists often turn to nature. For example, one fascinating aspect associated with certain plants is the rapid motion of such plants by a process called "explosive fracture." The explosive fracture of a plant involves rapid geometric changes of the plant that are induced by the tearing motion of the plant tissue for seed or sporangium dispersal. The rate of fracture explosion is significantly faster than that of the swelling motion of the plant tissue by several orders of magnitude due to the elastic instability of the plant tissue. As a result of this elastic instability, a critical point is reached when the plant's stored elastic energy overcomes constriction of the plant tissue, thereby inducing a high energy explosion. It can be appreciated that the fracture motion is easily detectable by the naked eye due to the dramatic changes in geometry. Hence, it is highly desirable to provide a method and device for detecting a material that mimics the explosive fracture of certain plants in order to generate a visual display for a user.

Therefore, it is a primary object and feature of the present invention to provide a method and device for detecting a material that is highly sensitive and selective, has a quick response time and generates few false alarms.

It is a further object and feature of the present invention to provide a method and device for detecting a material that is simple to use and is inexpensive to manufacture.

It is a still further object and feature of the present invention to provide a method and device for detecting a material that generates an easily observable signal to a user to indicate the presence of the material.

In accordance with the present invention, a detection device is provided for detecting a predetermined material. The device includes a first inner layer having first and second surfaces and a volume responsive to a first predetermined stimuli. The device also includes a second inner layer having first and second surfaces. An adhesive bonds at least a portion of the first surface of the first inner layer to the first surface of the second inner layer with a bonding force. A change in the volume of the first layer generates an elastic force on the adhesive material. The first inner layer delaminates from the second inner layer in response to the elastic force overcoming the bonding force.

The second inner layer has a volume responsive to the predetermined stimuli. In addition, the device also includes a first outer layer bonded to the first inner layer and having a volume responsive to a second predetermined stimuli. A second outer layer is bonded to the second inner layer and has a volume responsive to the second predetermined stimuli. A clip has a first end operatively connected to the first outer layer and a second end operatively connected to the second outer layer. The adhesive degrades in response to exposure to the predetermined material. It is contemplated for the first predetermined stimuli to be the predetermined material. The first and second inner layers include first and second ends. The adhesive is located adjacent the first ends of the first and second inner layers. A sheet, which does not bind with the inner layers, may be positioned between the first and second inner layers to reduce the bonding area so as to achieve faster reaction of the device.

In accordance with a further aspect of the present invention, a sensing mechanism is provided. The sensing mechanism includes a first inner layer having first and second surfaces and first and second ends. The first inner layer also has a volume responsive to a first predetermined stimuli. A second inner layer has first and second surfaces and first and second ends. The second inner layer also has a volume responsive to the first predetermined stimuli. An adhesive bonds the first surface of the first inner layer to the first surface of the second inner layer with a bonding force at a location adjacent the first ends of the first and second inner layers. Changes in the volumes of the first and second layers generate an elastic force on the adhesive material. The first inner layer delaminates from the second inner layer in response to the elastic force overcoming the bonding force.

A first outer layer is bonded to the first inner layer and has a volume responsive to a second predetermined stimuli. A second outer layer is bonded to the second inner layer and having a volume responsive to the second predetermined stimuli. A clip has a first end operatively connected to the first outer layer and a second end operatively connected to the second outer layer. The adhesive degrades in response to exposure to a predetermined material. A sheet is positioned between the first and second inner layers.

In accordance with a still further aspect of the present invention, a method of sensing for use in detecting a material is provided. The method includes the steps of interconnecting first and second inner layers with an adhesive and exposing the first and second inner layers to a solution. The first and second layers separate in response to material in the solution.

A first outer layer is bonded to the first inner layer and a second outer layer is bonded to the second inner layer. The first and second outer layers are interconnected with a clip. The adhesive degrades in response to exposure to the material and the first and second inner layers have a volume responsive to a predetermined stimuli. It is contemplated for the predetermined stimuli to be the material. The first and second inner layers generate an elastic force in response to the predetermined stimuli. The adhesive interconnects the first inner layer to the second inner layer with a bonding force. When the elastic force is greater than the bonding force in response to material in the solution, the first and second layers separate. A sheet may be positioned between a portion of the first and second inner layers.

BRIEF DESCRIPTION OF THE DRAWINGS

The drawings furnished herewith illustrate a preferred methodology of the present invention in which the above advantages and features are clearly disclosed as well as others which will be readily understood from the following description of the illustrated embodiment.

In the drawings.

DETAILED DESCRIPTION OF THE DRAWINGS

Figure 1:
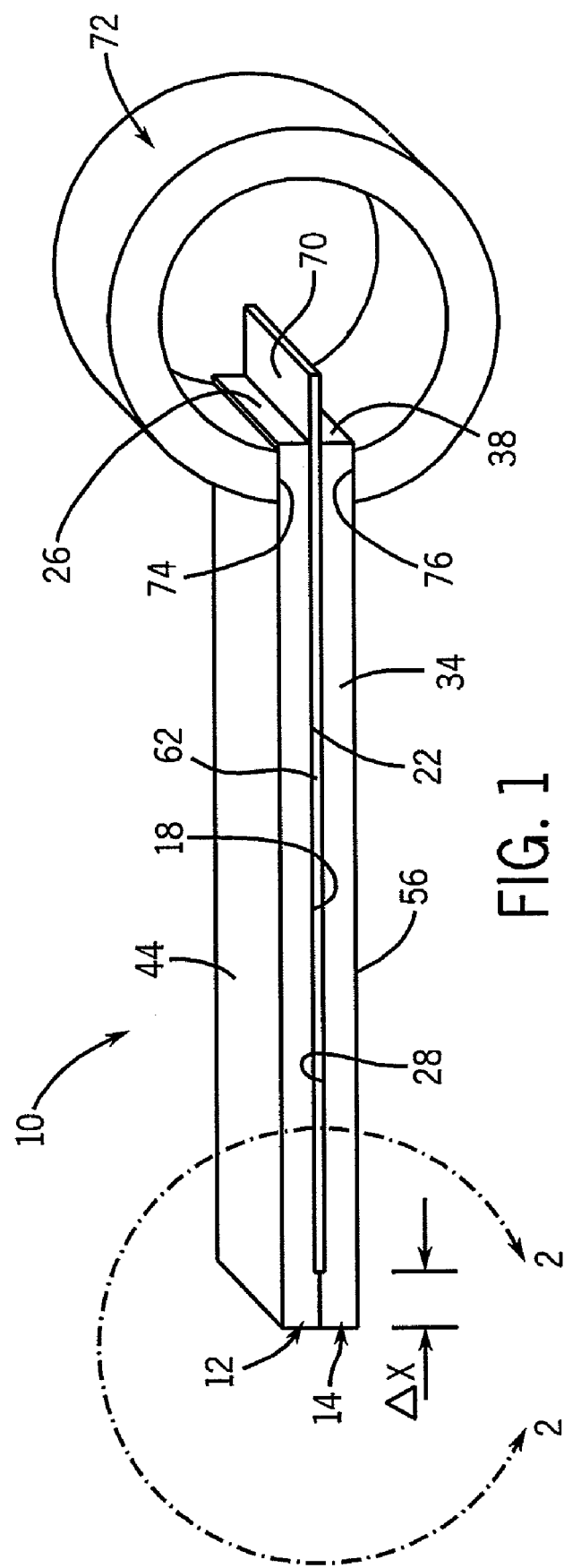
FIG. 1 is an isometric view of a detection device in accordance with the present invention.
Figure 2:
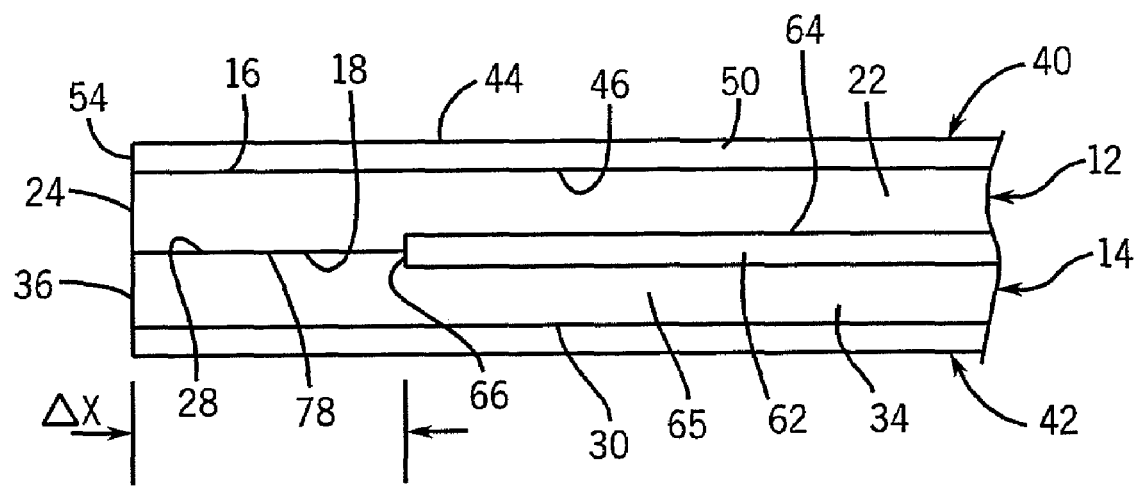
FIG. 2 is an enlarged, side elevational view show a portion the detection device of the present invention taken along line 2-2 of FIG. 1.
Figure 3:
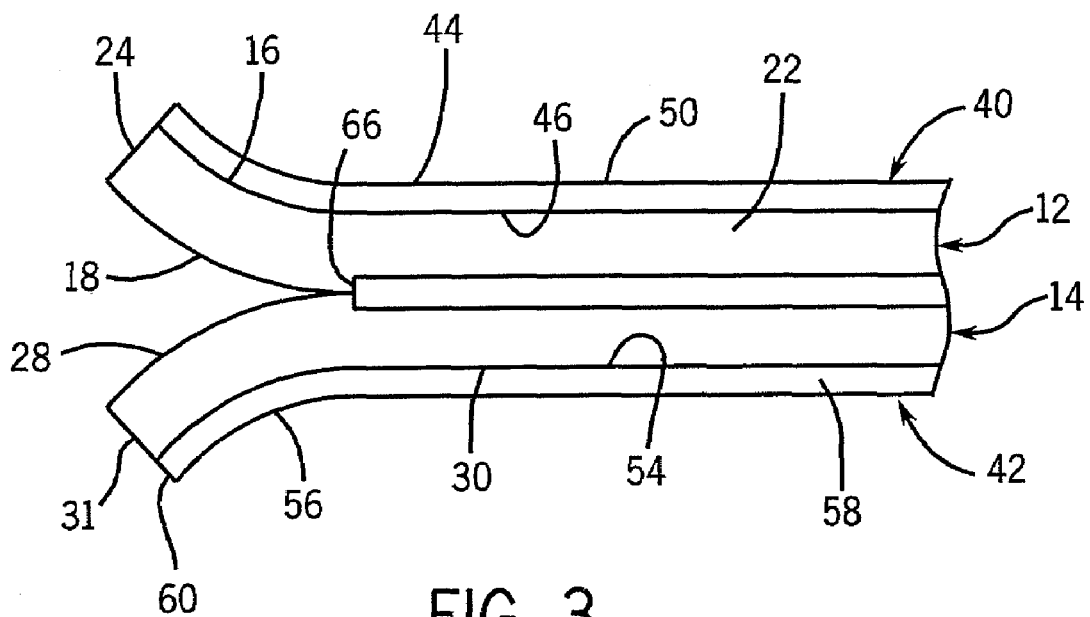
FIG. 3 is a side elevational view of the detection device of the present invention after actuation.

Referring to FIGS. 1-3, a detection device for detecting the presence of a material, such as a toxin or other chemical compound, in a solution is generally designated by the reference numeral 10. Detection device 10 includes first and second inner layers 12 and 14, respectively, fabricated from a hydrogel that swells in response to exposure to a predetermined stimuli. First inner layer 12 is defined by first and second surfaces 16 and 18, respectively, interconnected by first and second sides (not shown) and 22, respectively, and by first and second ends 24 and 26, respectively. Second inner layer 14 is defined by first and second surfaces 28 and 30, respectively, interconnected by first and second sides (not shown) and 34, respectively, and by first and second ends 36 and 38, respectively.

Detection device 10 further includes first and second outer layers 40 and 42, respectively, fabricated from a second hydrogel that swells in response to exposure to a predetermined stimuli. First outer layer 40 is defined by first and second surfaces 44 and 46, respectively, interconnected by first and second sides (not shown) and 50, respectively, and by first and second ends 52 and (not shown), respectively. Second surface 46 of first outer layer 40 is bonded to first surface 16 such that the sides and ends of first outer layer 40 are in registry with corresponding sides and ends of first inner layer 12.

Second outer layer 42 is defined by first and second surfaces 54 and 56, respectively, interconnecting by first and second sides (not shown) and 58, respectively, and by first and second ends 60 and (not shown), respectively. First surface 54 of second outer layer 42 is bonded to second surface 30 of second inner layer 14 such that the sides and the ends of second outer layer 42 are in registry with corresponding sides and ends of second inner layer 14.

A portion of second surface 18 of first inner layer 12 adjacent first end 24 is bonded to a first pre-determined portion of first surface 28 of second inner layer 14 adjacent first end 36 along a predetermined distance $\Delta X$. Second surface 18 of first inner layer 12 may be bonded to the first surface 28 of second inner layer 14 by means of an adhesive, by polarizing first and second inner layers 12 and 14, respectively, together or by an inherent stickiness of the hydrogels from which first and second inner layers 12 and 14, respectively, are fabricated. It can be appreciated that second surface 18 of first layer 12 and first surface 28 of second inner layer 14 are bonded together by a bonding force.

Detection device 10 further includes sheet 62 fabricated from a predetermined material preferably hydrophobic, e.g. polycarbonate. Sheet 62 is inserted between second surface 18 of first inner layer 12 and first surface 28 of second inner layer 14 at a location spaced from first ends 24 and 26 of corresponding first and second inner layers 12 and 14, respectively, by distance $\Delta X$. More specifically, sheet 62 includes a first surface 64 positioned against second surface 18 of first inner layer 12 and a second surface 65 positioned against first surface 28 of second inner layer 14. First end 66 of sheet 62 is positioned adjacent the bonded portions of first and second inner layers 12 and 14, respectively, so as to prevent the bonding of the entire second surface 18 of first inner layer 12 to first surface 28 of second inner layer 14. Second end 70 of sheet 62 projects from second ends 26 and 38 of corresponding first and second inner layers 12 and 14, respectively.

Detection device 10 further includes a generally C-shaped clip 72 or any tweezers type holder. C-shaped clip 72 includes a first generally flat terminal end 74 bonded to first surface 44 of first outer layer 40 and a second opposite terminal end 76 bonded to second surface 56 and second outer layer 42. Clip 72 is fabricated from a rigid material so as to allow a user to handle detection device 10 and to insert detection device 10 into a predetermined solution, as hereinafter described.

It is contemplated to fabricate detection device 10 using liquid phase photopolymerization. By way of example, a polycarbonate cartridge having an adhesive gasket seal around the edge is attached to a microscope slide and filled with a pre-polymer. A photomask representing the shapes of a plurality of layers of the detection device 10 is placed over the cartridge. The cartridge is exposed to UV light for a predetermined time period and a predetermined level of intensity to polymerize the pre-polymer. The cartridge is removed from the microscope glass slide, thereby leaving a plurality of layers of responsive hydrogels. A second cartridge, having twice the thickness, is attached on the glass slide so as to enclose the first set of layers of hydrogels. The cartridge is filled with a second pre-polymer and a photomask representing the shape of the detection devices is placed and aligned on top of the second cartridge. The second cartridge is exposed to UV light with a predetermined intensity for a predetermined time period to polymerize the second pre-polymer. The second cartridge is removed from the microscope glass slide and the bonded layers are cleaned with ethanol and nitrogen. Pairs of bonded layers are removed from the microscope glass slide and bonded together, as heretofore described, to form detection device 10.

By way of example, it is contemplated to fabricate first and second inner layers 12 and 14, respectively, from base responsive hydrogels. First and second outer layers 40 and 42, respectively, may be fabricated from acid responsive hydrogels. As a result, a user may inserting detection device 10 into a base buffer solution by means of clip 72, such that portions of first and second inners layers 12 and 14, respectively, bonded to each other are received in the solution. It can be appreciated that first and second inner layers 12 and 14, respectively, swell in response to exposure to the base buffer solution. As a result, first and second inner layers 12 and 14, respectively, generate an elastic force causing the first and second inner layers 12 and 14, respectively, to bend outwardly. The outward bending caused by the swelling of first and second inner layers 12 and 14, respectively, is constricted until the elastic force generated by the swelling of the first and second inner layers 12 and 14, respectively, overcomes the bonding force along the bonded portions of second surface 18 of first inner layer 12 and first surface 28 of second inner layer 14. Once the elastic force overcomes the bonding force, the bonded portions of first and second inner layers 12 and 14, respectively, delaminate, FIG. 3, and the first and second layers 12 and 14, respectively, bend outward.

It is contemplated to bond first and second inner layers 12 and 14, respectively, with an adhesive which is biodegradable or chemically sensitive and which dissolves in response to contact with certain types of chemicals, materials, or toxins. For example, adhesive 78 may dissolve in the presence of the specific material, resulting in the bending outward of first and second layers 12 and 14, respectively, as depicted in FIG. 3. In addition, it can be appreciated that the bonding force provided by adhesive 78 can be varied by increase or deceasing the predetermined distance ΔX along which first and second inner layers 12 and 14, respectively, are bonded. As a result, the response time at which the bonded portions of first and second inner layers 12 and 14, respectively, delaminate may be adjusted.

Figure 4:
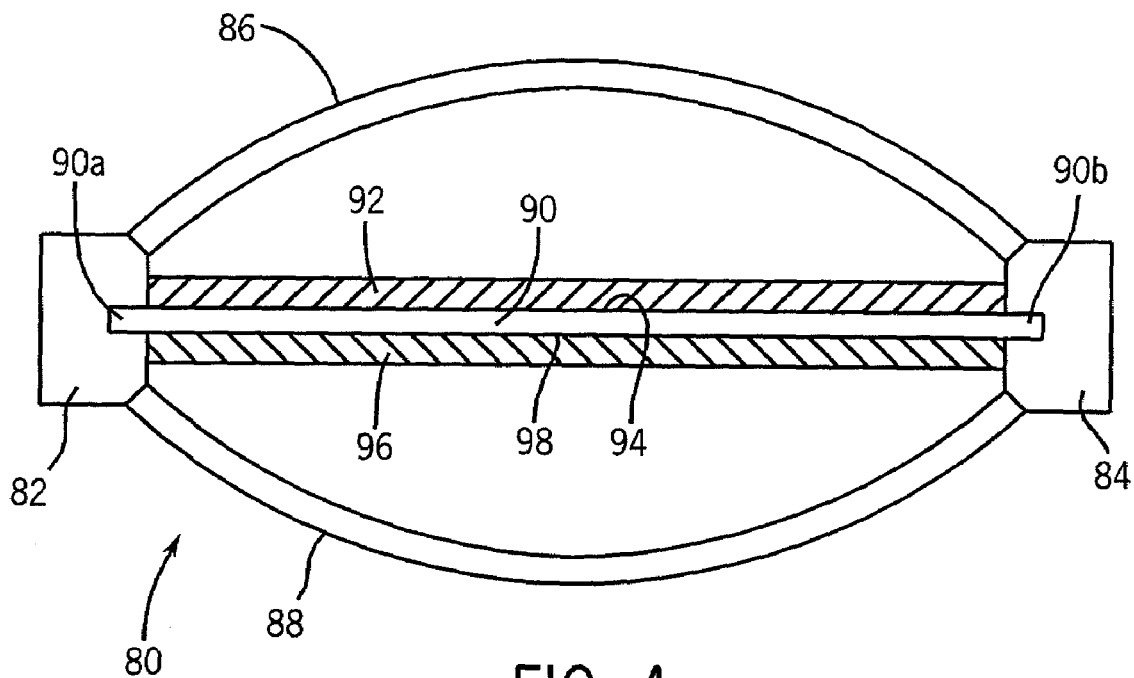
FIG. 4 is a side elevational view of an alternate embodiment of a detection device in accordance with the present invention.

Referring to FIG. 4, an alternate embodiment of a detection device in accordance with the present invention is generally designated by the reference numeral 80. Detection device 80 includes first and second supports 82 and 84, respectively, interconnected and spaced by rigid, generally arcuate rods 86 and 88. Flexible sheet 90 has a first end 90a secured to first support 82 and a second end 90b secured to second support 84. A first layer 92 fabricated from a hydrogel that swells in response to exposure to a first predetermined stimulus is bonded to upper surface 94 of sheet 90. A second layer 96 fabricated from a hydrogel that swells in response to exposure to a second predetermined stimulus is bonded to second surface 98 of sheet 90.

Figure 5:
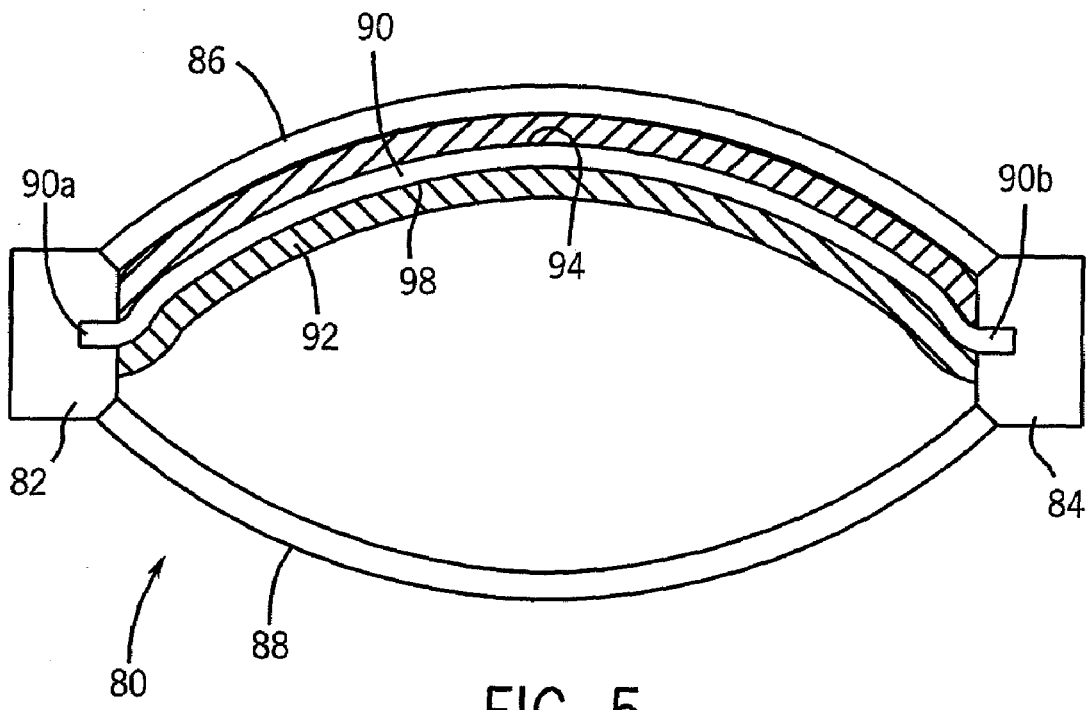
FIG. 5 is a side elevational view of the detection device of FIG. 4 after actuation.

It can be appreciated that as first layer 92 swells in response to the first predetermined stimulus, first layer 92, and hence flexible sheet 90, bends downwardly towards rod 88. Alternatively, as second layer 96 swells in response to the second predetermined stimuli, second layer 96, and hence flexible sheet 90, bends flexible sheet 90 toward rod 86, FIG. 5. It can be appreciated that first and second layers 92 and 96, respectively, may be responsive to predetermined specific materials. As a result, a detection device 80 may be used to simply and easily sense the presence of a specific material in a solution or the like.

Various modes of carrying out the invention are contemplated as being within the scope of the following claims particularly pointing out and distinctly claiming the subject matter that is regarded as the invention.

We claim:

1. A detection device for detecting a predetermined material, comprising:
    a first inner layer having first and second surfaces and having a volume, the volume being responsive to the predetermined material independent of a pressure on the first inner layer;
    a second inner layer having first and second surfaces and at least a portion of the first surface of the first inner layer bonded to the first surface of the second inner layer with a bonding force;
  wherein:
    a change in the volume of the first layer generates an elastic force on the at least the portion of the first surface; and
    the first inner layer delaminates from the second inner layer in response to the elastic force overcoming the bonding force.

2. The detection device of claim 1 further comprising:
    a first outer layer bonded to the first inner layer and having a volume responsive to a second predetermined stimuli; and
    a second outer layer bonded to the second inner layer and having a volume responsive to the second predetermined stimuli.

3. The detection device of claim 1 further comprising a sheet positioned between the first and second inner layers.

4. The detection device of claim 1 wherein the second inner layer has a volume responsive to a predetermined stimuli.

5. The detection device of claim 4 wherein the first predetermined stimuli is the predetermined material.

6. The detection device of claim 1 further comprising an adhesive for bonding the at least a portion of the first surface of the first inner layer to the first surface of the second inner layer and wherein the adhesive degrades in response to exposure to the predetermined material.

7. The detection device of claim 6 wherein the first and second inner layers include first and second ends, the adhesive located adjacent the first ends of the first and second inner layers.

8. A sensing mechanism, comprising:
    a first inner layer having first and second surfaces and first and second ends, the first inner layer having a volume responsive to a first predetermined stimuli independent of pressure on the first inner layer; and
    a second inner layer having first and second surfaces and first and second ends, the second inner layer having a volume responsive to the first predetermined stimuli independent of pressure on the first inner layer, the first surface of the first inner layer bonded to the first surface of the second inner layer with a bonding force adjacent the first ends of the first and second inner layers;
  wherein:
    a change in the volumes of the first and second layers generates an elastic force; and
    the first inner layer delaminates from the second inner layer in response to the elastic force overcoming the bonding force.

9. The sensing mechanism of claim 8 further comprising:
    a first outer layer bonded to the first inner layer and having a volume responsive to a second predetermined stimuli; and
    a second outer layer bonded to the second inner layer and having a volume responsive to the second predetermined stimuli.

10. The sensing mechanism of claim 8 further comprising an adhesive for bonding the first surface of the first layer to the first surface of the second inner layer and wherein the adhesive degrades in response to exposure to a predetermined material.

11. The sensing mechanism of claim 8 further comprising a sheet positioned between the first and second inner layers.

12. A method of sensing for use in detecting a material, comprising the steps of:

interconnecting first and second inner layers with a bonding force; and exposing the first and second inner layers to a solution; wherein the first and second layers expand in response to the material in the solution such that the first and second layers separate.

13. The method of claim 12 comprising the additional steps of:

bonding a first outer layer to the first inner layer; and bonding a second outer layer to the second inner layer.

14. The method of claim 12 wherein the first and second inner layers generate an elastic force in response to the material and wherein the elastic force is greater than the bonding force in response to material in the solution such that the first and second layers separate.

15. The method of claim 12 comprising the additional step of positioning a sheet between a portion of the first and second inner layers.

16. A detection device for detecting a predetermined material, comprising:

a first inner layer having first and second surfaces and having a volume responsive to a first predetermined stimuli;

a second inner layer having first and second surfaces and at least a portion of the first surface of the first inner layer bonded to the first surface of the second inner layer with a bonding force;

a first outer layer bonded to the first inner layer and having a volume responsive to a second predetermined stimuli;

a second outer layer bonded to the second inner layer and having a volume responsive to the second predetermined stimuli;

a clip having a first end operatively connected to the first outer layer and a second end operatively connected to the second outer layer; and wherein:

a change in the volume of the first inner layer generates an elastic force on the at least the portion of the first surface; and the first inner layer delaminates from the second inner layer in response to the elastic force overcoming the bonding force.

17. A sensing mechanism, comprising:

a first inner layer having first and second surfaces and first and second ends, the first inner layer having a volume responsive to a first predetermined stimuli; and a second inner layer having first and second surfaces and first and second ends, the second inner layer having a volume responsive to the first predetermined stimuli, the first surface of the first inner layer bonded to the first surface of the second inner layer with a bonding force adjacent the first ends of the first and second inner layers;

a first outer layer bonded to the first inner layer and having a volume responsive to a second predetermined stimuli; and a second outer layer bonded to the second inner layer and having a volume responsive to the second predetermined stimuli;

a clip having a first end operatively connected to the first outer layer and a second end operatively connected to the second outer layer;

wherein:

a change in the volumes of the first and second inner layers generate an elastic force; and the first inner layer delaminates from the second inner layer in response to the elastic force overcoming the bonding force.

18. A method of sensing for use in detecting a material, comprising the steps of:

interconnecting first and second inner layers with a bonding force;

exposing the first and second inner layers to a solution;

bonding a first outer layer to the first inner layer;

bonding a second outer layer to the second inner layer; and interconnecting the first and second outer layers with a clip;

wherein the first and second inner layers separate in response to material in the solution.

19. A method of sensing for use in detecting a material, comprising the steps of:

interconnecting first and second inner layers with a bonding force; and exposing the first and second inner layers to a solution; wherein:

the first and second layers are bonded by an adhesive that dissolves in response to exposure to the material; and the first and second layers separate in response the dissolving of the adhesive.

* * * * *

UNITED STATES PATENT AND TRADEMARK OFFICE
CERTIFICATE OF CORRECTION

PATENT NO.        : 7,562,562 B2                                        Page 1 of 1
APPLICATION NO.   : 11/745855
DATED             : July 21, 2009
INVENTOR(S)       : David J. Beebe et al.

It is certified that error appears in the above-identified patent and that said Letters Patent is hereby corrected as shown below:

Please amend the "Reference to Government Grant" clause found in column 1, beginning at line 4, to read as follows:

-- This invention was made with United States government support awarded by the following agencies: NAVY/ONR N00014-04-1-0659. The United States government has certain rights in this invention. --

Signed and Sealed this

Third Day of November, 2009

David J. Kappos
*Director of the United States Patent and Trademark Office*